United States Patent [19]

Warner et al.

[11] Patent Number: 5,601,420

[45] Date of Patent: Feb. 11, 1997

[54] INTERLOCK, LATCHING, AND RETAINING MECHANISM FOR AN INFUSION PUMP

[75] Inventors: Eric A. Warner, Vista; Don S. Minami, Monte Sereno; Paul L. Howard, Palo Alto; Phillip M. Hobson, Los Altos, all of Calif.

[73] Assignee: IVAC Medical Systems, Inc., San Diego, Calif.

[21] Appl. No.: 305,468

[22] Filed: Sep. 12, 1994

[51] Int. Cl.⁶ .................................................. F04B 43/08
[52] U.S. Cl. .................. 417/474; 417/477.1; 417/477.2; 417/360; 604/153; 128/DIG. 12; 73/756
[58] Field of Search .......................... 417/474, 63, 477.1, 417/477.2, 360, 238; 604/153; 128/DIG. 12; 73/19.1, 753, 754, 756

[56] References Cited

U.S. PATENT DOCUMENTS

| | | | |
|---|---|---|---|
| 4,199,307 | 9/1980 | Jassawalla | 417/474 |
| 4,236,880 | 12/1980 | Archibald | 417/478 |
| 4,273,121 | 6/1981 | Jassawalla | 128/214 F |
| 4,276,004 | 6/1981 | Hahn | 417/479 |
| 4,303,376 | 12/1981 | Siekmann | 417/360 |
| 4,493,706 | 1/1985 | Borsanyi et al. | 604/153 |
| 4,519,792 | 5/1985 | Dawe | 604/152 |
| 4,657,490 | 4/1987 | Abbott | 417/478 |
| 4,696,671 | 9/1987 | Epstein et al. | 604/67 |
| 4,735,558 | 4/1988 | Kienholz et al. | 417/477 |
| 4,842,584 | 6/1989 | Pastrone | 604/50 |
| 4,857,048 | 8/1989 | Simons et al. | 604/50 |
| 5,056,992 | 10/1991 | Simons et al. | 417/474 |
| 5,074,756 | 12/1991 | Davis | 417/45 |
| 5,290,239 | 3/1994 | Classey et al. | 128/DIG. 12 |
| 5,302,093 | 4/1994 | Owens et al. | 417/474 |
| 5,322,422 | 6/1994 | Natwick et al. | 417/474 |

OTHER PUBLICATIONS

Brochure–The AVI 200 and Micro 210 Infusion Pumps with the Unique AVI Cassette.

*Primary Examiner*—Charles G. Freay
*Attorney, Agent, or Firm*—Fulwider Patton Lee & Utecht, LLP

[57] ABSTRACT

An interlock, latching and retaining mechanism for use in an infusion system, embodying a latch arm mounted to a rotatable shaft having a plurality of cams and gears attached thereto, a rectangular faceplate with a plurality of apertures formed therethrough, and a clamp. Rotating the latch arm functions to engage fluid monitoring, flow control and pumping structure of the infusion system with a pumping segment for control of fluid flow through the segment and also causes the clamp to hold the pumping segment in a required position. In another aspect, rotation of the latch arm additionally causes an air-in-line sensor to rotate into position on the pumping segment.

42 Claims, 10 Drawing Sheets

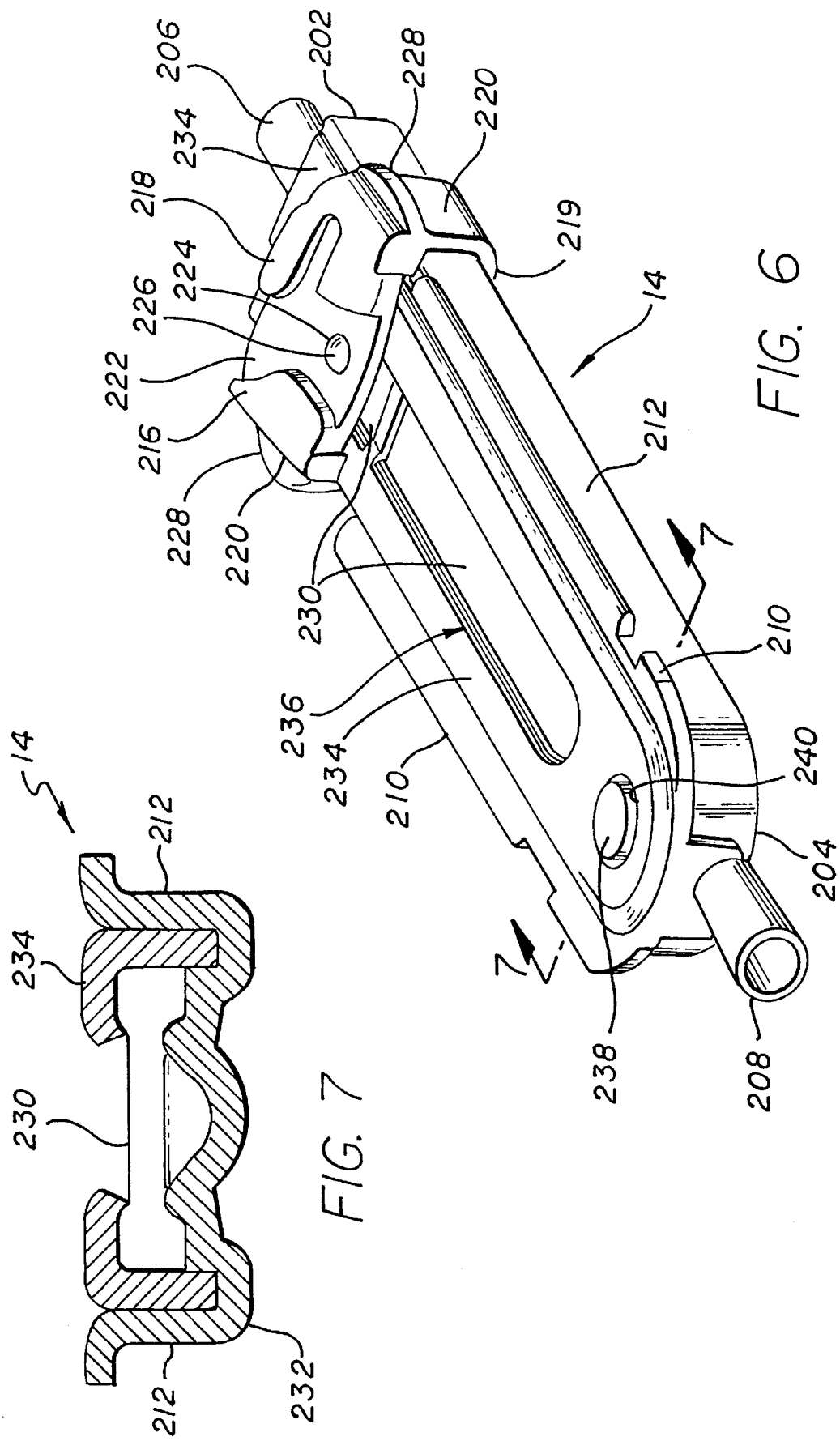

INTERLOCK, LATCHING, AND RETAINING MECHANISM FOR AN INFUSION PUMP

BACKGROUND OF THE INVENTION

This invention relates generally to fluid infusion systems and, more particularly, to a new and improved novel latching and retaining mechanism for use in such systems which, upon manipulation of a single latch arm, operates to load a pumping segment into the infusion system and to place pumping, flow control and fluid line monitoring structures of the infusion system into engagement with the pumping segment.

The infusion of fluids into a patient is usually accomplished by means of an infusion administration set in conjunction with controlling apparatus that meters the rate of flow of fluid through the set. Peristaltic type pumps, which function by repetitively occluding successively adjacent sections of tubing in a wave-like motion, have proven particularly attractive for use in controlling fluid flow. They operate externally on the fluid conduits to pump the fluids to the patient and therefore, do not introduce contamination into the system. Additionally, they provide increased precision of control over the fluid flow through the system.

Typically in such systems, a pressure plate provides a rigid surface against which the fluid conduit is pressed while the peristaltic fingers progressively occlude the conduit. The rigid surface is located in a predetermined position for consistency in the pumping operation and may be either spring loaded or fixed in relation to the front of the pump. Should the surface move from the expected position or move outside the expected range of movement, the quantity of fluid pumped may be altered from that desired. It is thus important to provide an accurate mounting structure for holding the pressure plate in a known position.

Due to the environment in which infusion systems may be used, it is often desirable to control or at least limit the pressure within the fluid delivery conduit providing fluid to the patient. When the pressure in the conduit exceeds a predetermined limit, some pumping systems will stop the operation of the pump. Accordingly, some infusion systems incorporate a pressure sensor for monitoring the fluid pressure in the fluid delivery conduit. These pressure sensors rely on correct positioning in relation to the conduit to be sensed, to insure accuracy. Thus, it is desirable to provide a mounting system so that the pressure sensor correctly interfaces with the fluid conduit.

Likewise, it is often important to detect the presence of air in a fluid flow line. Some infusion systems employ structures and associated control systems to monitor a part of the administration set conduit for the presence and quantity of air. Proper positioning of the conduit in the sensor is essential for accuracy in the air-in-line measurement process. Positioning the conduit in the sensor prior to the beginning of the pumping operation is important and providing a mechanism that assists the pump operator in doing so is desirable.

In the case where a fluid conduit segment has a manual flow control device for manual flow control of fluid flow through the conduit (such as for priming) and has a device for peristaltic pump flow control, some interaction with these mechanisms and the peristaltic pump system must occur. For example, free flow through the conduit from the reservoir to the patient is avoided with peristaltic pumps in that at least one peristaltic finger is always occluding the conduit at all times. However, before the conduit is mounted to the peristaltic pump system, a manual flow control device, usually termed a "flow stop" is used to prevent free flow. If the manual flow stop is made a part of the conduit pumping segment, it is desirable to have the peristaltic fingers occlude the conduit before the manual flow stop is moved to the flow position, so that free flow does not occur inadvertently.

In the case where a pumping segment is provided that includes a flow control valve, such as a slide mechanism for manual control over the fluid flow, a pumping section which peristaltic fingers massage to move fluid, a pressure sensing section for engagement with a pressure sensor, and a tubing section that mounts in an air-in-line sensor, ease and reliability in correctly mounting the pumping segment is desirable. Additionally, configuring the pumping segment and interfacing mechanisms of the pumping mechanism so that the pumping segment is properly mounted before the flow control is positioned to permit flow, and so that the pressure sensor and air-in-line sensor engage the appropriate sections of the pumping segment before pumping can begin is desirable.

Hence, those skilled in the art have long recognized the need for an improved interlock, latching and retaining mechanism that receives a pumping segment, retains that segment in the correct position, and locks the segment in a predetermined position so that correct pumping action can occur. There is also a recognized need for a mechanism that times the engagement of the peristaltic mechanism with the pumping segment and the release of the manual flow stop so that an undesired free flow condition is avoided. Also recognized is a need to assist in correctly locating a portion of the pumping segment in an air-in-line sensor before operation of the pumping mechanism. The present invention fulfills all of these needs.

SUMMARY OF THE INVENTION

Briefly, and in general terms, the present invention provides a new and improved interlock, latching, and retaining mechanism for an infusion system that functions to quickly, reliably and simply load into the infusion system a pumping segment for fluid flow. Further, the interlock, latching and retaining mechanism functions to similarly load pumping, flow control and fluid line monitoring structure of the infusion system into engagement with the pumping segment. Additionally, certain features of the infusion system and pumping segment maybe interlocked together for correct operation during loading.

The interlock, latching, and retaining mechanism of the present invention accomplishes expeditious loading by employing structure cooperating with the pumping, flow control and fluid line monitoring structure of the infusion system and the pumping segment, for placing the infusion system structure and the pumping segment into desirable operating positions. Generally, this is accomplished, in accordance with the invention, by manipulation of a single latch arm embodied in the interlock, latching and retaining mechanism.

In a presently preferred embodiment, by way of example and not necessarily by way of limitation, the interlock, latching and retaining mechanism includes a latch arm, a clamp and a shaft, each of which are rotatably attached to a faceplate. The faceplate provides structure for receiving the pumping segment, as well as provides apertures through which the various functions of the infusion system can be performed. The shaft is adapted to respond to the manipulation of the latch arm and has gears and cams attached thereto which cooperate with the clamp and flow control and fluid line monitoring structures of the infusion system to place them into proper operating position. The clamp functions to releasably retain the pumping segment against the faceplate.

Additionally, the latching and retaining mechanism of the present invention functions to ensure proper sequencing of operation and avoidance of undesired free flow conditions. The interlock, latching and retaining mechanism is constrained to receiving the pumping segment with its flow control structure in a "flow stop" position. Upon placement of the pumping segment within the interlock, latching and retaining mechanism and upon manipulation of the latch arm, the clamp is configured to hold the pumping segment. Further, the interlock, latching and retaining mechanism functions to place pumping structure of the infusion system into operating position, wherein the pumping structure occludes fluid flow through the pumping segment, prior to causing the flow control structure of the pumping segment to be placed into its final position for allowing normal operational flow. In addition, upon so manipulating the latch arm, the interlock, latching and retaining mechanism operates to place the fluid monitoring structure of the infusion system in operating position as well as communicates to the infusion system that a pumping segment has been received by the interlock, latching and retaining mechanism. In one particular aspect, the interlock, latching and retaining mechanism functions to cause rotation of an air-in-line sensor into operating position.

Hence, the present invention satisfies the needs for a new and improved interlock, retaining and latching mechanism which, upon manipulation of the single latch arm, enables an infusion system to be quickly, reliably and simply initialized for pumping, flow control and monitoring of fluid passing through a pumping segment.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIG. 6 is a perspective view of the pumping segment shown in FIG. 1 that is releasably retained by the interlock, latching and retaining mechanism of FIG. 3;

FIG. 7 is a cross-sectional view of the pumping segment of FIG. 5, taken along the line 7—7 in FIG. 5;

DETAILED DESCRIPTION OF THE PREFERRED EMBODIMENTS

Figure 1:
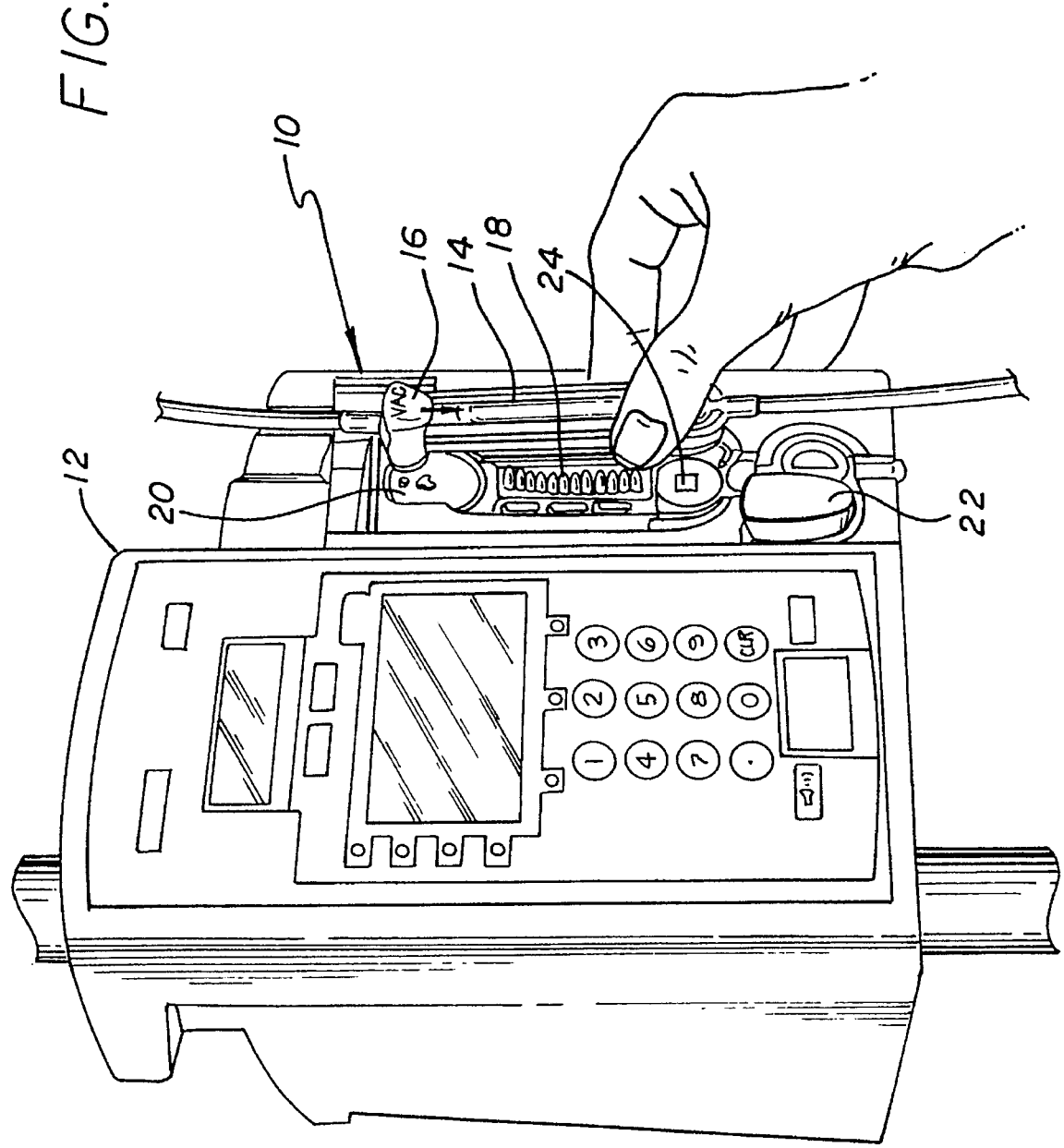
FIG. 1 is a front perspective view of a pumping apparatus constructed in accordance with the present invention, and illustrates an interlock, latching and retaining mechanism attached to an infusion system adapted to receive a pumping segment.

As is shown in the drawings, which are included for purposes of illustration and not by way of limitation, and wherein like reference numerals denote like or corresponding views throughout the drawings, the invention is embodied in an interlock, latching and retaining mechanism which functions to correctly load a unique pumping segment for fluid flow into an infusion system as well as load pumping, flow control and fluid line monitoring structure of the infusion system into appropriate operating positions.

Referring now more particularly to FIG. 1, there is shown an interlock, latching and retaining mechanism 10 constructed in accordance with the present invention. As may be appreciated from FIG. 1, the interlock, latching and retaining mechanism 10 is incorporated into an infusion system 12 and is adapted to receive an associated pumping segment 14. The pumping segment 14 is configured for fluid flow and connects a reservoir (not shown) containing infusate to a patient. Generally, the pumping segment 14 includes flow control structure 16 that must be placed in a "flow stop" position prior to placing the segment 14 into the infusion system 12. The infusion system 12 controls the delivery of the infusate to the patient and includes a pumping structure 18, a flow control structure 20, an air-in-line sensing structure 22 and a pressure sensing structure 24, each of which cooperate with associated structure of the pumping segment 14. The interlock, latching and retaining mechanism 10, in turn, cooperates with the pumping structure 18 and the air-in-line sensing structure 22 of the infusion system 12, as well as receives the pressure sensing structure 24 of the infusion system 12, each of which are placed into operating position before pumping of fluid through the pumping segment 14 (that has been received by the interlock, latching and retaining mechanism 10) is attempted. Further, the interlock, latching and retaining mechanism 10 cooperates with the flow control structure 20 of the infusion system 12 to thereby cause the flow control structure 16 of the pumping segment 14 to be placed in a position to allow fluid flow. It is to be noted that the flow control structure 16 of the pumping segment 14 is placed in a position for allowing flow subsequent to placing pumping structures 18 of the infusion system 12 into operating position. This avoids free flow conditions.

Figure 2:
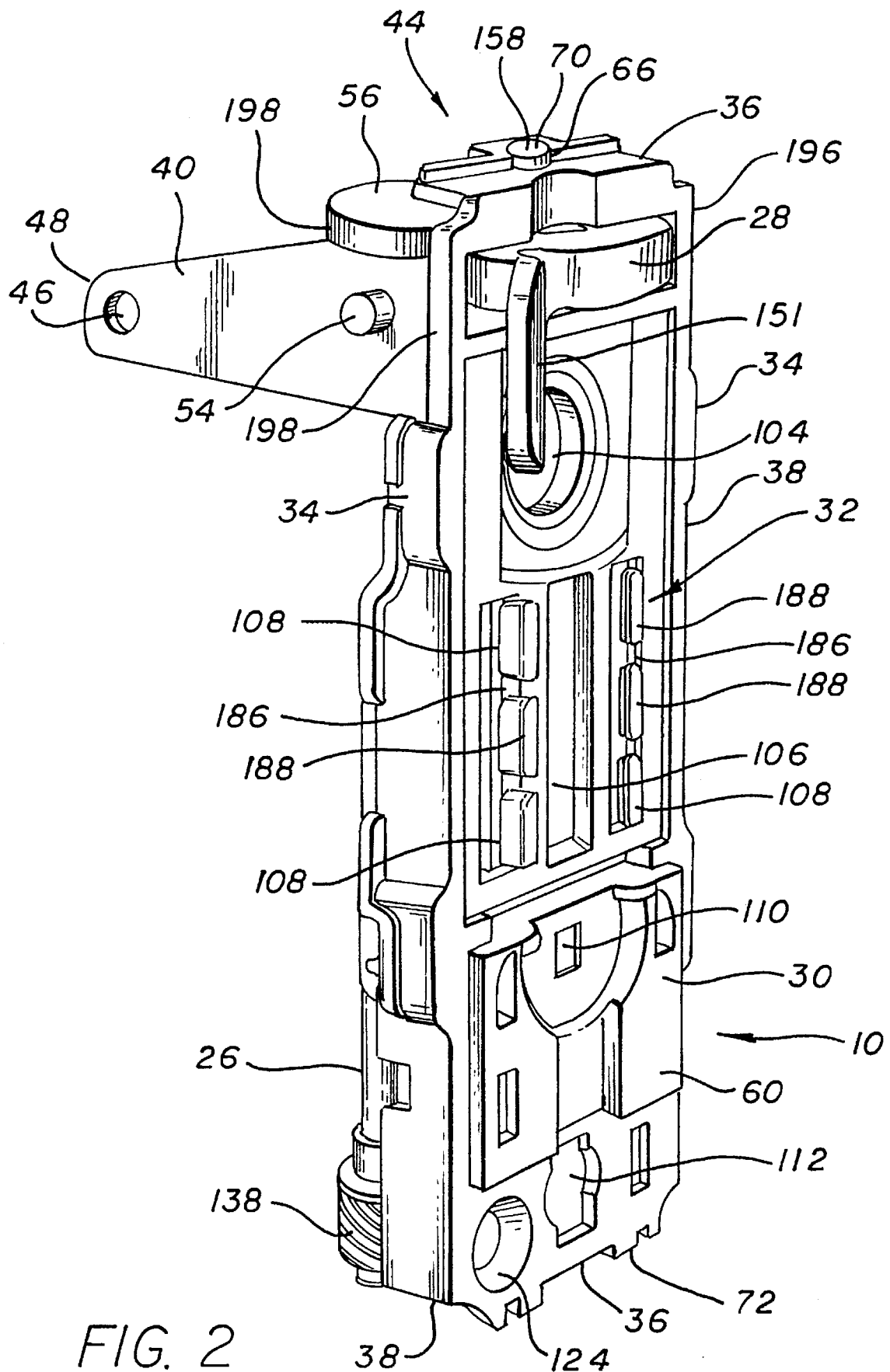
FIG. 2 is a front perspective view illustrating the interlock, latching and retaining mechanism of FIG. 1 in a closed configuration and detached from the infusion system.
Figure 3:
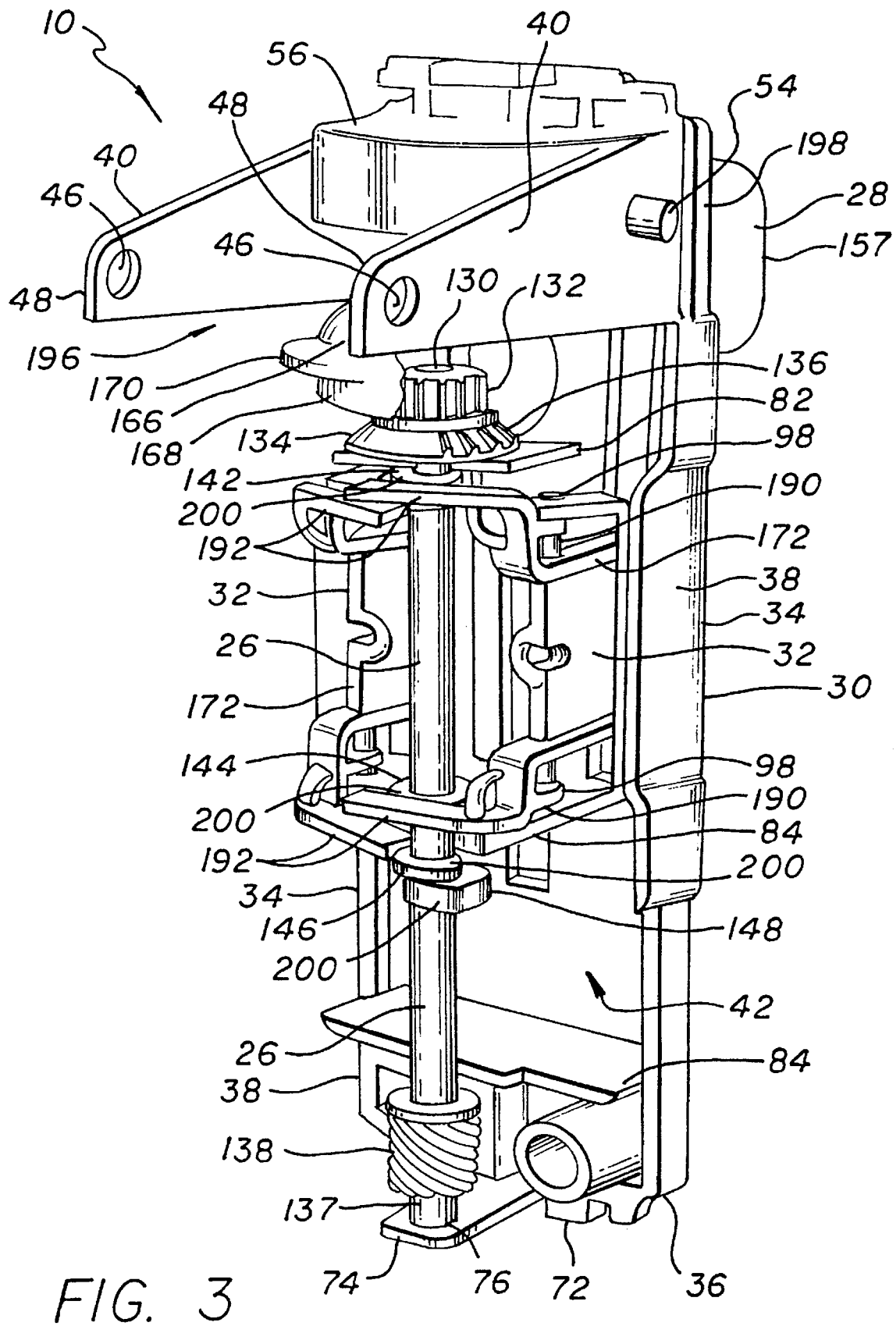
FIG. 3 is a perspective view of the rear surface of the apparatus shown in FIG. 2.

Referring to FIGS. 2 and 3, there is shown a presently preferred embodiment of the interlock, latching and retaining mechanism 10 constructed in accordance with the present invention. As best seen in FIG. 3, the interlock, latching and retaining mechanism 10 includes a shaft 26, a latch arm 28, a rectangular faceplate 30 and a clamp 32. Generally, the shaft 26 and latch arm 28 are each rotatably mounted to the faceplate 30 and are mechanically linked to each other so that by manipulating the latch arm 28, the shaft 26 rotates. Further, the clamp 32 is pivotally mounted to the faceplate 30 and configured to cooperate with the shaft 26 so that, upon rotation of the shaft 26 the clamp 32 is allowed to open and close so as to releasably engage the pumping segment 14. Finally, the faceplate 30 includes structure for attaching the interlock, latching and retaining mechanism 10 to the infusion system 12 so that the pumping 18, air-in-line 22, flow control 20 and pressure sensing 24 structure of the infusion system 12 may be placed in proper engagement with the interlock, latching and retaining mechanism 10.

Figure 4:
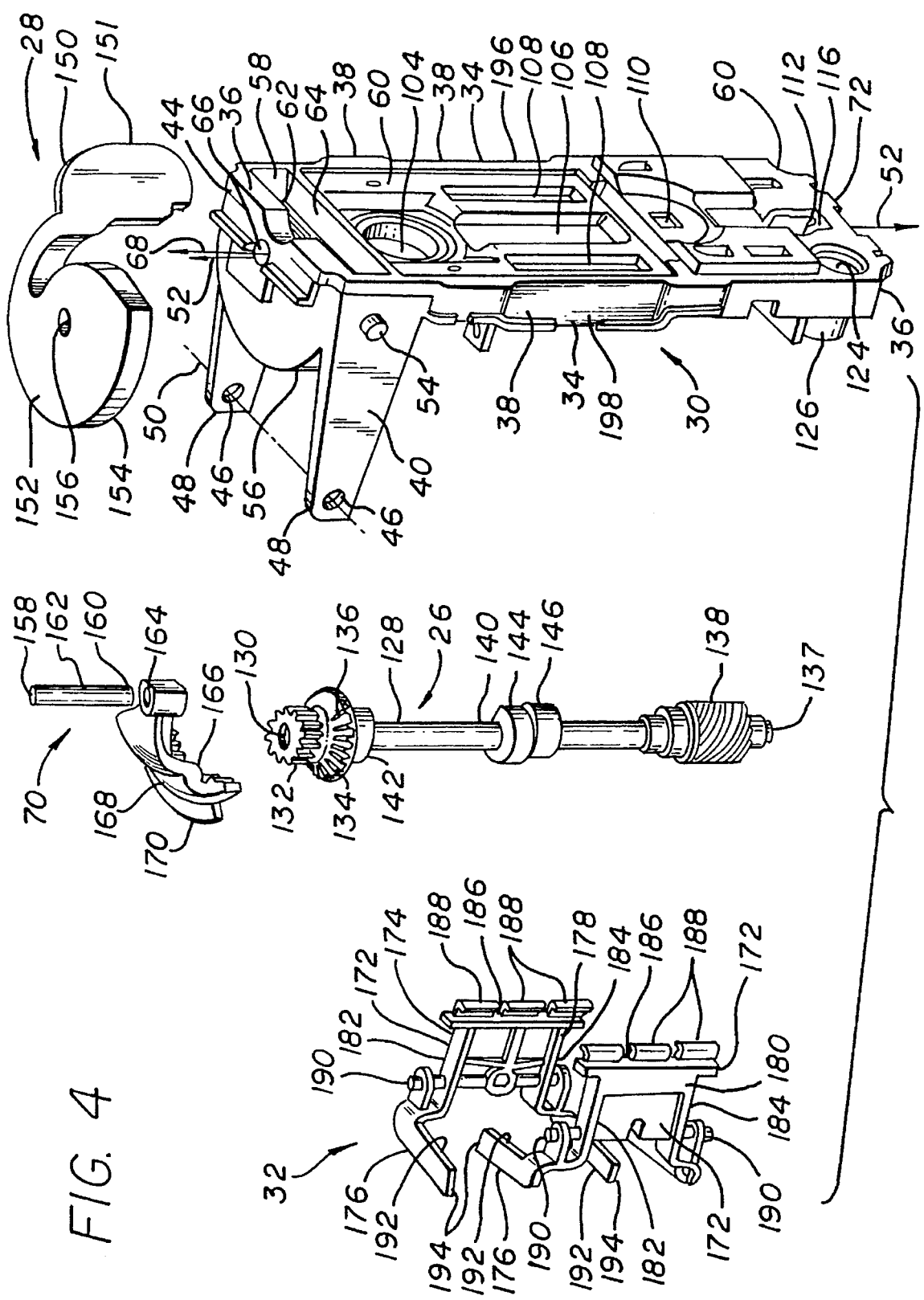
FIG. 4 is an exploded, perspective view of the interlock, latching and retaining mechanism shown in FIG. 2.

As shown in FIG. 4, the faceplate 16 is generally rectangular in shape and has two long sides 34, two short sides 36 and a perimeter 38. The faceplate 30 includes two spaced apart arms 40 extending substantially perpendicularly from a rear surface 42 near a top 44 of the faceplate 30. Further, the arms 40 are spaced apart so that they each individually extend from the rear surface 42 near the portion of the perimeter 38 defining the long sides 34 of the faceplate 30. Each arm 40 includes a through hole 46 near their terminal ends 48 which is adapted to receive associated structure of the infusion system 12. An axis 50 extending through the through holes 46 is parallel to the faceplate 30 and perpendicular to a long axis 52 of the faceplate 30. Additionally, projecting laterally outward from the arms 40 and perpendicularly to the long axis 52 of the faceplate 30 are bosses 54. There is one boss 54 to each arm 40 and each are similarly positioned upon the arms 40. That is, each boss 54 is positioned near the connection of the arm 40 to the faceplate 30.

Extending laterally across the rear surface 42 near the top 44 of the faceplate 30 and between the spaced apart arms 40 is a hollow semicircular projection 56. A lateral rectangular latch aperture 58 formed in a front side 60 of the faceplate 30 defines an opening to the hollow semicircular projection 56. This hollow semicircular projection 56 provides the latch arm 38 with a cavity for rotation, Formed in upper and lower walls 62 and 64 of the semicircular projection 56 are latch rod holes 66 (FIG. 4 only shows the latch rod hole formed in the upper wall 62). An axis 68 extending through the latch rod holes 66 is parallel to the long axis 52 of the faceplate 30. It is to be noted that the latch rod holes 66 are adapted to receive a latch rod 70 (also shown in FIG. 4), upon which the latch arm 28 rotates.

Figure 5:
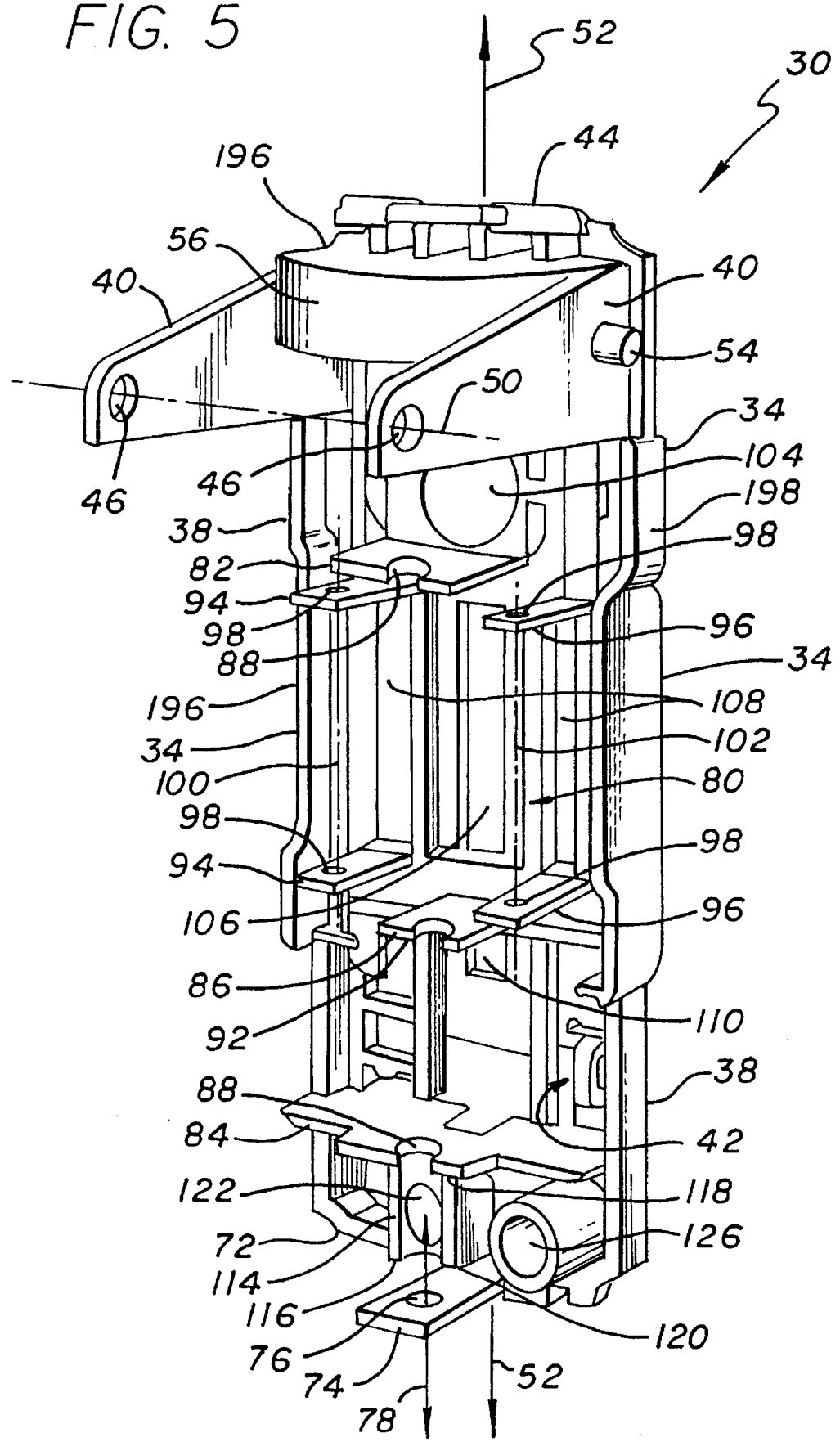
FIG. 5 is a perspective view of the faceplate included in FIG. 4, showing the rear structure of the faceplate.

Referring to FIG. 5, extending perpendicularly from the rear surface 42 near a bottom 72 and along the long axis 52 of the faceplate 30 is a receiving member 74 for the shaft 26. Formed in the shaft receiving member 74 is a through hole 76 that has an axis 78 extending therethrough that is parallel to the long axis 52 of the faceplate 30. Projecting from a midsection 80 of the rear surface 42 and along the long axis of the faceplate 30 are three spaced apart members 82, 84, 86 for supporting the shaft 26 when it is affixed to the faceplate 30. The midsection member 82 positioned closest to the top 44 of the faceplate 30 includes a notch 88 formed therein for receiving and engaging the shaft 26. Simarly, the midsection member 84 positioned closest to the bottom 72 of the faceplate 30 and the midsection member 86 formed between the other midsection members 82, 84 include a notch 88 for engaging and supporting the shaft 26.

Also projecting perpendicularly from the rear surface 42 of the faceplate 30, are first 94 and second 96 pairs of clamp supporting members. The pairs of supporting members 94, 96 form a rectangular pattern on the rear surface 42 of the faceplate 30, wherein the pairs 94, 96 of supporting members form the corners of the rectangular pattern. The individual members of the first pair 94 are spaced longitudinally apart. Similarly, the individual members of the second pair 96 are spaced longitudinally apart. Further, the first and second pairs 94, 96 are spaced equal lateral distances from the center or long axis 52 of the faceplate 30. Formed in each pair of the supporting members 94, 96 are through holes 98 adapted to receive structure of a clamp 32. It is to be noted that an axis 100 extending through the holes 98 formed in the first pair of supporting members 94 and an axis 102 extending through the holes 98 formed in the second pair of supporting members 96 are each parallel to the long axis of the faceplate 30.

The faceplate 30 also includes various apertures formed therein (see FIG. 4). The rectangular latch aperture 58 which is positioned near the top 44 of the faceplate 30 has already been described. A circular fluid regulation aperture 104 centered in the width of the faceplate 30 is positioned just below the rectangular latch aperture 58. Centered in the face plate 30 below the circular fluid regulation aperture 104 and extending longitudinally along the long axis 52 of the faceplate 30 is a rectangular pump finger aperture 106. On either side of the pump follower aperture 106 are a pair of longitudinally extending rectangular clamping finger apertures 108. Directly below the pumping follower aperture 106 and also centered in the width of the faceplate 30 is a square pressure sensor aperture 110.

Further, formed into the faceplate 30 near its bottom 72 are two further apertures that each have associated structure projecting from the rear surface of the faceplate 30 (best seen in FIG. 5). A longitudinally elongate and irregularly-shaped aperture 112 is formed in the faceplate 30 substantially along the long axis 52 of the faceplate 30. Formed within the irregularly shaped aperture 112 is a vertical backwall 114 and a horizontal bottom wall 116. The vertical backwall 114 is attached at its upper end 118 to a bottomside of the midsection member 84 positioned closest to the bottom 72 of the faceplate 30 and at its bottom end 120 to the horizontal bottom wall 116. In addition, formed in the vertical backwall 114 is an oval-shaped hole 122.

Located at approximately the same longitudinal location along the faceplate 30 and next to the irregularly shaped aperture 112 is a circular air sensing aperture 124. Extending from the circular air sensing aperture 124 and projecting perpendicularly from the rear surface 42 of the faceplate 30 is a cylindrical sidewall 126.

Referring again to FIG. 4, the shaft 26 is cylindrical in shape and has various gearing and camming surfaces affixed to its exterior 128. Affixed to a top end 130 of the shaft 26 is a conventional straight tooth gear 132. Affixed to the shaft 26 immediately adjacent to and just below the straight tooth gear 132 is a bevel gear 134. In the preferred embodiment, the bevel gear 134 has teeth 136 about approximately 50% of its circumference. The rest of the circumference is without teeth 136. The bevel gear 134 is configured upon the shaft 26 with its smallest diameter positioned closest to the top end 118 of the shaft 26. Located near a bottom end 137 of the shaft 26 is a third gear 138. The third gear 138 is a crossed helical gear and has curved and inclined teeth 112.

Spaced longitudinally apart along a midsection 140 and affixed to the shaft 26 are three cams 142, 144, 146. A first cam 142 is positioned proximal to and below the bevel gear 134. A second cam 144 is below and spaced apart from the first cam 144. A third cam 146 is proximate and below the second cam 144.

As shown in FIG. 4, the latch arm 28 is generally shaped like a "g" with an additional latch projection 150 extending away from the "head" and approximately at a right angle to the "tail" of the g-shaped latch arm. The latch projection includes a downwardly extending extension 151 which is directed substantially perpendicularly to upper and lower surfaces 152, 154 of the latch arm 28. A hole 156 is formed in the "head" of the g-shaped latch arm 28 and is adapted to fixedly receive the latch rod 70.

The latch rod 70, also shown in FIG. 4, is cylindrical in shape and has a top end 158 and a bottom end 160. As previously stated, the latch rod 70 is configured to be received in the shaft holes 66 formed in the upper and lower walls 62, 64 of the latch aperture 56. The top end of 158 of the latch rod 70 may be threaded or otherwise conventionally configured for fastening it to the faceplate 30. A midsection 162 is adapted to fixably retain the latch arm 28. The bottom end 160 of the latch rod 70 is adapted to be attached to an approximately a one quarter portion of a gear ring 166. The gear ring 166 includes a receiving hole 164 into which the latch rod 70 is placed with an interference fit. About an outer circumference 168 of the gear ring 166 is formed a wall 170 which extends substantially perpendicularly to the outer circumference 168.

As best seen in FIG. 4, the clamp 32 includes two opposing members 172, each of which are substantially identical in shape. Each opposing member 72 includes a first portion 174 lying substantially perpendicular to a second portion 176. The first portion 174 includes inside and outside surfaces 178, 180 and terminal end 186 that is perpendicular to the upper and lower perimeters 182, 184. Extending from the terminal end 186 and parallel to the upper and lower perimeters 182, 184 of the first portion 174 are three spaced apart clamping fingers 188. Extending perpendicularly outward from each of the upper and lower perimeters 182, 184 is a peg 190 about which the members 172 pivot. The second portion 176 of the opposing members 172 includes two parallel spaced apart arms 192 each extending substantially perpendicularly from the first portion 174. The spaced apart arms 192 are adapted to engage and cooperate with the first and second cams 142, 144 respectively.

Refer again to FIGS. 2 and 3, wherein the components of the interlock, latching and retaining mechanism 10 are shown in their assembled form. In an assembled interlock, latching and retaining mechanism 10, to mount the latch arm 28 to the latch rod 70 the bottom end 160 of the latch rod 70 is inserted through the latch rod hole 66 formed in the upper wall 62 of the semicircular projection 56. It will be appreciated from FIGS. 2 and 3 that the head of the g-shaped latch arm 28 is then placed within the semicircular projection 56 with its downwardly pointing extension 151 directed towards the bottom 72 of the faceplate 30 and the bottom end 160 of the latch rod 70 is inserted through the hole 156 formed in the latch arm 28. Next, the bottom end 160 is inserted through the latch rod hole 66 formed in the lower wall 64 of the semicircular projection 56. Thereafter, the bottom end 160 of the latch rod 70 is then fixedly placed into the receiving hole 164 of the gear ring 166. Finally, using conventional means, the latch rod 70 is rotatably mounted within the latch rod hole 66 formed in the upper wall 62.

In placing the latch arm 28 upon the latch rod 70, particular attention is paid to the relative orientations of the latch arm 28 and the ring gear 166 attached to the bottom end 160 of the latch rod 70. The latch arm 28 is attached to the latch rod 70 so that the latch arm 28 of the assembled interlock, latching and retaining mechanism 10 is positioned in its fully closed position when a terminal end of the wall 170 formed on the outer circumference 168 of the gear ring 166 engages the rear surface 42 of a right side 196 of the front 60 of the faceplate 30. That is, the latch arm 28 and latch rod 70 are properly oriented where the latch arm 28 is completely swung to a left side 198 of the faceplate 30 when the gear ring 166 is completely swung to the right side 196.

Particular attention is also paid to the relative orientations of the clamp 32 and the faceplate 30 of the assembled interlock, latching and retaining mechanism 10. It will be appreciated from FIGS. 2 and 3 that the clamp 32 is attached to the faceplate 30 so that each of the terminal ends 186 of the pair of opposing members 172 of the clamp 32 project through one of the pair of pump finger apertures 108 respectively and so that each of the spaced apart arms 192 point toward the faceplate long axis 52 or towards that center of the faceplate 30. Once the clamp is so oriented, the pegs 188 formed on each of the opposing numbers 172 of the clamp 32 are placed into the through holes 98 formed in the supporting members 94, 96 extending from the rear surface 42 of the faceplate 30.

Referring to FIG. 3, the shaft 26 is rotatably mounted to the rear surface 42 of the faceplate 30 by inserting the bottom end 137 of the shaft 26 into the through hole 76 formed in the receiving member 74 extending from the bottom 72 of the rear surface 42 of the faceplate 30. Generally, the shaft 26 is mounted to the rear surface 42 of the faceplate 30 so that it cooperates with the clamp 32, the rear surface 42 of the faceplate 30 and the gear ring 166 attached to the latch rod 70. With the latch arm 28 in its closed position, the straight tooth gear 132 affixed to the top end 130 of the shaft 26 is placed within the gear ring 166 so that the portion of the bevel gear 134 that lacks teeth 136 faces away from the rear surface 42 of the faceplate 30. When the shaft is so oriented, the raised portions 200 of the first, second and third cams 142, 144, 146 point away from the rear surface 42 of the faceplate 30. In addition, when the shaft 26 is attached to the faceplate 30 the shaft 26 engages mid-section members 182, 184, 186 extending from the rear surface 42 of the faceplate 30.

As mentioned, the pumping segment 14 may be releasably retained by the interlock, latching and retaining mechanism 10. That is, the clamp 32 operates to retain the pumping segment 14 against the faceplates 30 when the latch arm 28 is closed, but is releasably retained in that as the latch arm 28 is rotated to its open position, the shaft 26 cooperates with the clamp 32 to allow it to pivot and thereby release the pumping segment 14. Further, the pumping segment 14 is to cooperate with an infusion system 12 which functions to control the transfer of fluid from a reservoir to a delivery site. The infusion system 12 delivers fluid from the reservoir to a proximal end 202 (see FIG. 6) of the pumping segment 14 by way of conventional tubing. The fluid passes through the pumping segment 14 and exits a distal end 204 (see FIG. 6) of the pumping segment 14. Attached to the distal end 204 may be additional conventional tubing of the infusion system that transports the fluid away from the pumping segment 14 and towards a delivery site.

Referring to FIG. 6, the engineered pumping segment 14 is generally elongate in shape. Extending from the proximal end 202 of the elongate pumping segment 14 is a cylindrical tubing fitting 206 that is adapted to attach to conventional tubing (not shown) of the infusion system and that defines an entrance for the passage of fluid into the pumping segment 14. Similarly, extending from the distal end 204 is another cylindrical tubing fitting 208 that also is adapted to attach to conventional tubing of a pumping system and that defines an exit port for fluid passing through the pumping segment 14. The pumping segment 14 also includes a flange 210 extending substantially perpendicularly from the top of a sidewall 214 of the pumping segment 14. The flange 210 is formed about the distal end 204 and on either side of the midsection of the pumping segment 14 and terminates at parallel longitudinal locations on either side of the pumping segment 14. The engineered pumping segment 14 also includes a slider 216. The slider 216 is adapted to fit around and travel longitudinally along a portion of the pumping segment 14 near its proximal end 202. The slider 216 has a first long side 218 and a second long side 219 and a pair of short sides 220 completing its generally rectangular cross-sectional shape. Formed in substantially the center of the first long side 218 is a groove 220. Formed within the groove 220, is a socket 222 which is adapted to receive and retain a ball bearing 226. Further, formed into the short sides 220 and extending the length of the slider 216 and substantially perpendicularly therefrom, are rounded low-profile projections or ears 228.

As is best seen in FIG. 7, the engineered pumping segment 14 includes an elastomeric membrane 230 that is sandwiched between a base 232 and a cover 234. Generally, the path that fluid takes through the pumping segment 14 is defined by the membrane 230 and base 232. The cover 234 generally functions to sealingly retain the membrane 230 against the base 232 as well as against itself.

In cooperation with the interlock, latching and retaining mechanism 10 and the infusion system 12, the pumping segment 14 performs three different functions. Referring again to FIG. 6, near the proximal end 202 of the engineered pumping segment 14 there is structure functioning to regulate flow rates through the pumping segment 14 In an intermediate section 236 of the pumping segment 14 there is structure adapted to cooperate with the infusion system 12 to peristaltically pump fluids through the pumping segment 14 Near its distal end 204, the pumping segment 14 has structure adapted to cooperate with the infusion system 12 to sense the pressure of fluid passing through the pumping segment 14.

Fluid flow regulation is generally accomplished in the pumping segment 14 through the use of the slider 216 which cooperates with associated structure of the infusion system. Near the proximal end 202 of the pumping segment 14 the cover 234 provides access to the elastomeric membrane 230. By way of the access provided by the cover 234, the ballbearing 226 functions to depress the membrane 234 into the fluid flow path, whereby the cross-sectional area through which fluid may flow is altered. As the slider 216 travels along the base 232 it depresses the membrane 230 into the flow path to varying degrees. By altering the fluid flow path and by doing so to varying degrees, the slider 216 regulates the flow of fluid through the pumping segment 14.

Turning now to the peristaltic pumping of fluids through the pumping segment 14, peristaltic pumping is facilitated primarily through the cooperation of the membrane 230 and cover 234 of the pumping segment 14. At the intermediate section 236 of the pumping segment 14, the cover 234 provides further access to the membrane 230, through which a peristaltic pumping mechanism (not shown) of the infusion system 12 operates. Generally, the peristaltic pumping mechanism operates to sequentially depress adjacent portions of the membrane 230 into the fluid flow path to thereby advance fluid through the pumping segment 14.

Pressure sensing of fluids flowing through the pumping segment 14 is facilitated primarily through the cooperation of the membrane 230 and cover 234 of the pumping segment 14. Near the distal end 204 of the pumping segment 14, the cover 234 again provides access to the membrane 230. In this area, the membrane 230 is formed into a generally hollow and flexible dome-shaped pressure vessel 238 with a cylindrical sidewall 240 which acts as a pressure diaphragm for transferring pressure information regarding fluid flowing through the pumping segment 14.

Figure 8:
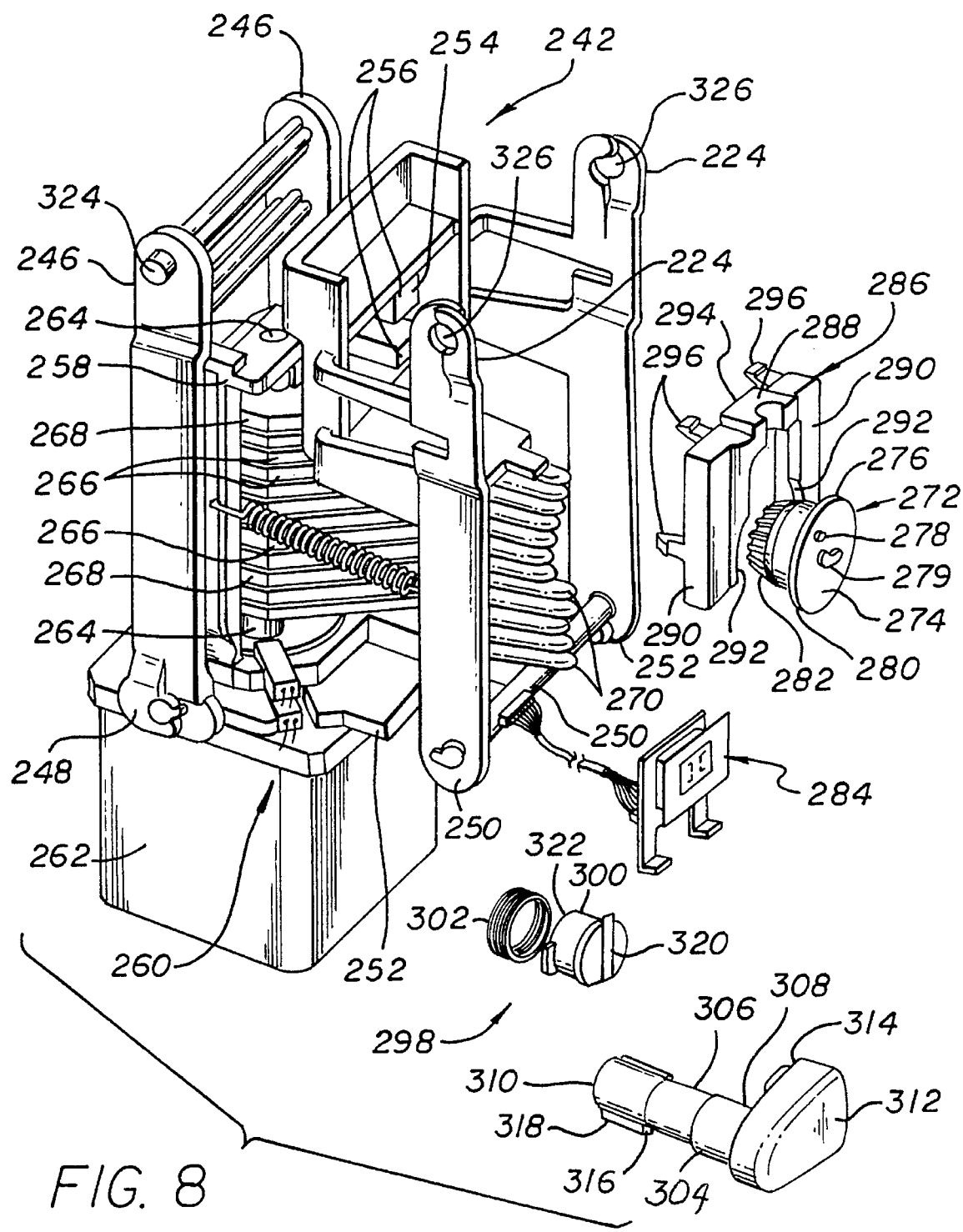
FIG. 8 is an exploded perspective view of components of the infusion system which are attached to the interlock, latching and retaining mechanism.

Referring to FIG. 8, the infusion system 12 includes a frame 242 to which the interlock, latching and retaining mechanism 10 is attached. The frame 242 includes a first vertical portion 244 and a second vertical portion 246 which are connected at their bottoms 248, 250 (respectively) by a horizontal portion 252. The first vertical portion 246 is adapted to be mounted proximal to the rear surface 42 of the faceplate 30. The second vertical portion 246 is adapted to be mounted to the arms 40 extending from the rear surface 42 of the faceplate 30. The second vertical portion 246 is also adapted to include structure to which a photo-detector 254 is mounted. The photo-detector 254 is configured to transmit light energy between two spaced apart members 256 embodying the detector 254 and to receive the wall 170 extending from the outer circumference 168 of the gear ring 166.

The horizontal portion 252 includes an upwardly extending vertical frame 258. The vertical frame 258 is adapted to retain a peristaltic pumping mechanism 260. The peristaltic pumping mechanism 260 includes a motor 262 that extends below the horizontal portion 252. Extending upwardly and within the vertical frame 258 is a motor shaft 264 that is driven by the motor 262 and that cooperates with a plurality of fingers 266. The fingers 266 are mounted side by side within the vertical frame 258 substantially perpendicularly to the motor shaft 264 and are slidably retained by their first end 268 within the vertical frame 258. A second end 270 of the fingers 266 is adapted to project through the finger aperture 108 formed in the faceplate 30. It is to be noted that as the motor shaft 264 is caused to rotate, the fingers 266 alternatively rise and fall in a perpendicular motion to the motor shaft 264.

The interlock, latching and retaining mechanism 10 also interacts with a flow control actuator 272 (see FIG. 8) of the infusion system 12 that is adapted to be retained by the faceplate 30. The flow control actuator 272 has a front surface 274 that has a circular perimeter 276. Extending from the front surface 274 is a cylindrical projection 278 and an irregularly shaped projection 279. A back surface 280 of the flow control actuator 272 includes a bevel gear 282 over 80% of the circumference projecting away from and perpendicularly to the front surface 274.

Further, the interlock, latching and retaining mechanism 10 receives a pressure sensor 284 of the infusion system 12 (see FIG. 8). The pressure sensor 284 is adapted to be retained within the square pressure aperture 110 and to sense pressure existing within the pumping segment 14. Moreover, the interlock, latching and retaining mechanism 10 receives a curtain 286 that is adapted to assure that the slider 216 is placed in its flow stop position prior to the placement of the pumping segment 14 within the clamp 32. The curtain 286 includes a horizontal portion 288 connecting two spaced apart downwardly directed portions 290. Formed into the downwardly directed portions 290 are cut-outs 292 which receive the ears 228 formed into the slider 216. Extending from a rear side 294 of the curtain 286 are projections 296 which aid in attaching the curtain 286 to the faceplate 30.

Finally, the interlock, latching and retaining mechanism 10 interacts with an air-in-line sensor 298 of the infusion system 12. The air-in-line sensor 298 includes a first housing 300 which cooperates with a spring 302 and a second housing 304. Generally, the second housing 304 includes an elongate portion 306 having first 308 and second 310 ends. Attached to the first end 308 is a sideways extending projection 312 the underside 314 of which is adapted to engage conventional tubing. The second end 310 includes a helical gear 316 comprising a segment of a circle and having curved and inclined teeth 318. The first housing 300 includes a front surface 320 for engaging conventional tubing and a back surface 322 that is adapted to receive forces applied by the spring 302. Contained within each of the first and second housings 300, 304 are transducers (not shown), one for transmitting ultrasonic energy and the other for receiving ultrasonic energy.

Figure 9:
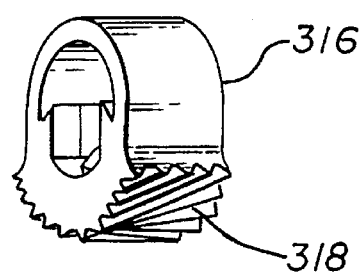
FIG. 9 is an enlarged perspective view of one of the components shown in FIG. 8.

Referring now to FIG. 9, there is shown an enlarged view of the helical gear 316 detached from the second housing 304. As clearly depicted in FIG. 9, the helical gear 316 has curved and inclined teeth 318. It is to be noted that the helical gear 316 cooperates with the third gear 138 attached to the bottom end 137 of the shaft 26 so that upon rotation of the shaft 26 the second housing 304 rotates to thereby place the sideways extending projection 312 into and out of operating position.

Figure 10:
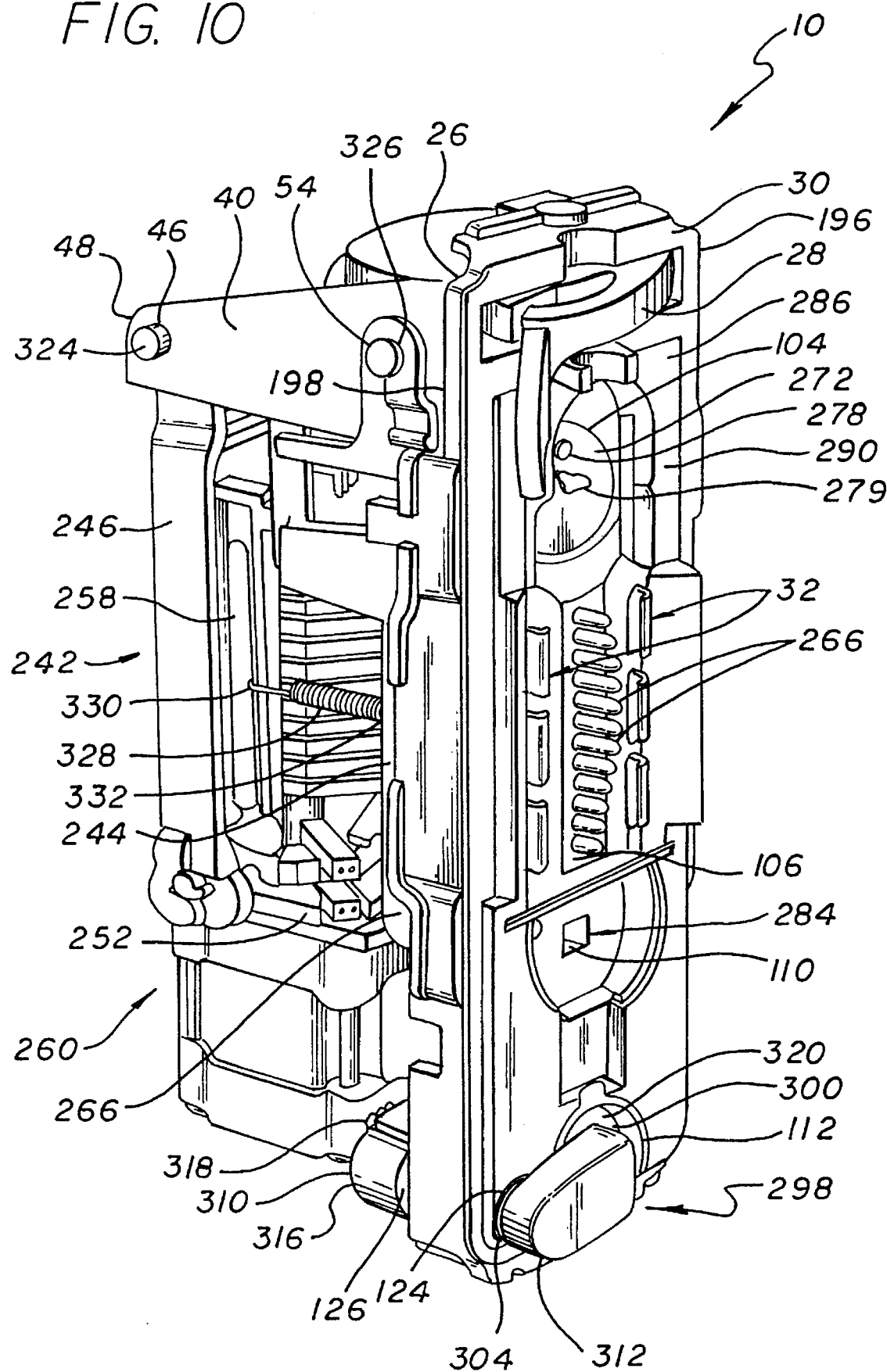
FIG. 10 is a perspective view of the interlock, latching and retaining mechanism of FIG. 3 in a closed configuration and incorporating the components of FIG. 8.

Referring to FIG. 10, the interlocking, latching and retaining mechanism 10 may be attached to the frame 242 and may incorporate the previously described components of the infusion system 12. In order to attach the interlock, latching and retaining mechanism 10 to the frame 242, the through holes 46 formed near the terminal ends 48 of the pair of arms 40 extending from the rear surface 42 of the faceplate 30 each receive a laterally extending projection 324 formed on the first vertical portion 244 of the infusion system frame 242. Moreover, the bosses 54 extending from each arm 40 are received in holes 326 formed in the second vertical portion 246 of the frame 242. Through these points of connection, the interlock, latching and retaining mechanism 10 is attached to the frame 242 of the infusion system 12. When the interlock, latching and retaining mechanism 10 is so attached, the fingers 266 of the peristaltic pumping mechanism 260 mounted to the frame 242 extend through the pump fingers aperture 108. By extending through the pump fingers aperture 108, the pump fingers 266 provide direct visual display of the pumping operating of the pumping mechanism 260. To maintain this visual display, it is contemplated that the pumping segment 14 be comprised of clear material so that the pumping operation of the pumping mechanism 260 can be observed when the pumping segment 14 is placed in the interlock, latching and retaining mechanism 10.

It will also be appreciated from FIG. 10, that the sliding flow control actuator 272 is to be inserted into the circular fluid regulation aperture 104 formed into the faceplate 30. The flow control actuator 272 is oriented so that the projections 278 extending therefrom project through the front side 60 of the faceplate 30 and so that the projections 278 are substantially vertically aligned when the latch arm 28 is in its closed position. Also, the bevel gear 282 (not shown) of the flow control actuator 272 is oriented so that its teeth are interspaced between the teeth of the bevel gear 138 (not shown) affixed to the shaft 26. Moreover, the curtain 286 is received in the faceplates 30 just below the latch arm 28 with its downwardly directed portions 290 substantially straddling the flow control actuator 272. In the preferred embodiment, it is contemplated that the projections 296 extending from the rear side 294 (not shown) of the curtain 286 snap into associated receptacles (not shown) of the faceplate 30.

Further, as is shown in FIG. 10, the first housing 300 of the air-in-line sensor 298 is fixedly placed within the irregularly shaped aperture 112. The spring 302 (not shown) is first placed within the irregularly shaped aperture 112 and is placed between the vertical backwall 114 (not shown) of the irregularly shaped aperture 112 and a back surface 322 (not shown) of the first housing 300. The front surface 320 of the first housing 300 is accessible through the irregularly shaped aperture 112. Moreover, the second housing 304 is placed within the circular air sensing aperture 124. The second housing 304 is oriented so that the second end 310 of the elongate portion 306 extends through the cylindrical sidewall 126 of the circular aperture 124 so that the helical gear 316 formed thereon engages the third gear 138 (not shown) located near the bottom end 137 of the shaft 26 (not shown). Additionally, the second housing 304 is oriented so that, when the latch arm 28 of the interlock, latching and retaining mechanism 10 is in its closed position, or where it is rotated to the left side 198 of the faceplate 30, the sideways extending projection 312 of the second housing 304 overlays the front surface 320 of the first housing 300.

As is shown in FIG. 10, the pressure sensor 284 placed in the square pressure aperture 110 with its pressure sensing surface accessible through the front side 60 of the faceplate 30. Moreover, also shown in FIG. 10 is a spring 328 that is attached at a first end 330 to the upwardly extending vertical frame 258 of the horizontal portion 252 of the frame 242 at its second end 332 to the first portion 174 (not shown) of the clamp 32. A second spring 392 (not shown) is similarly positioned on an opposite side of the interlock, latching and retaining mechanism 10. The springs 328 operate to bias the clamp 32 to a closed configuration and provide the force for occluding flow through the pumping segment 14 when the latch arm 28 is closed.

Figure 11:
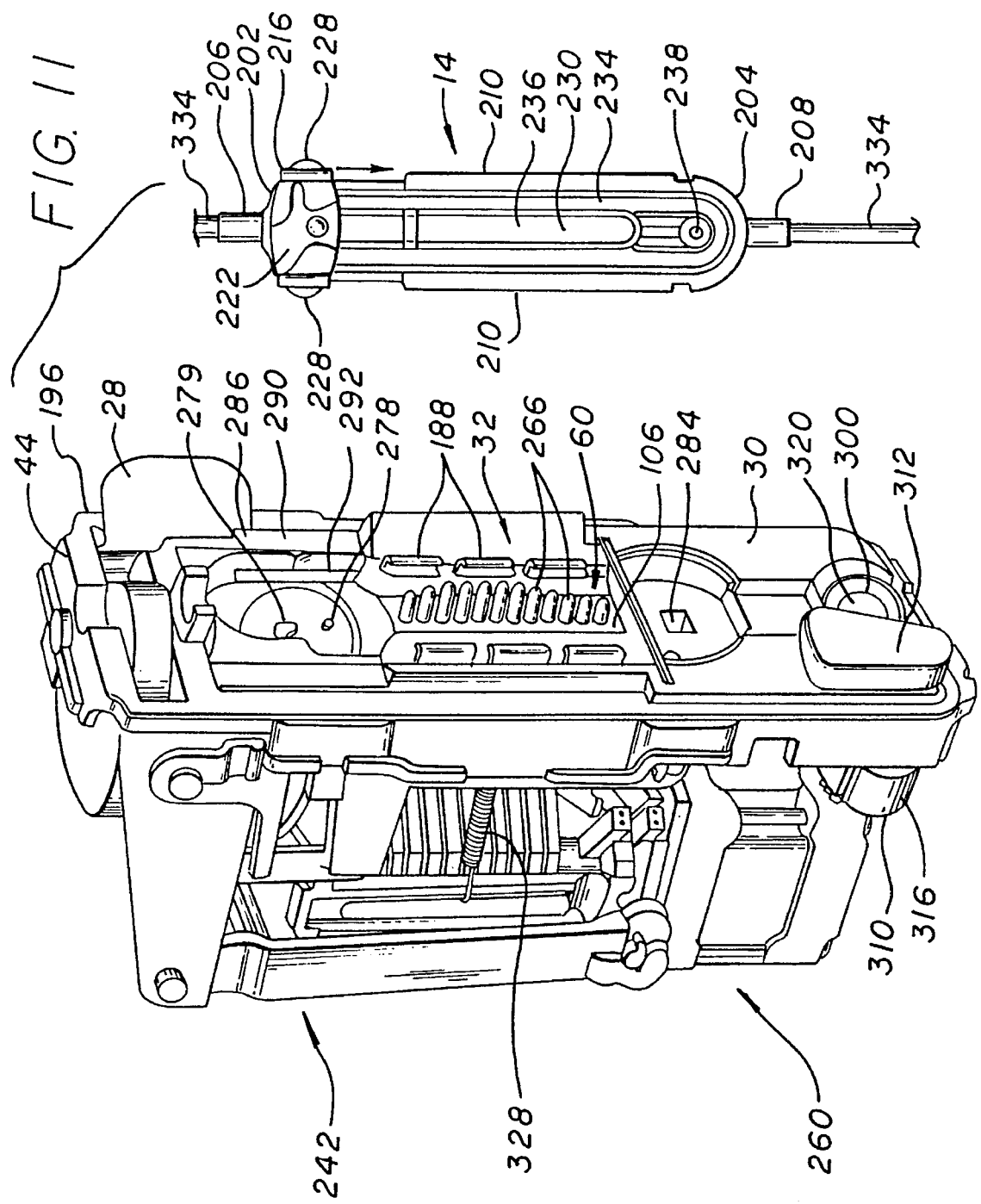
FIG. 11 is a perspective view of the interlock, latching and retaining mechanism of FIG. 10 in an open configuration and the pumping segment of FIG. 6.
Figure 12:
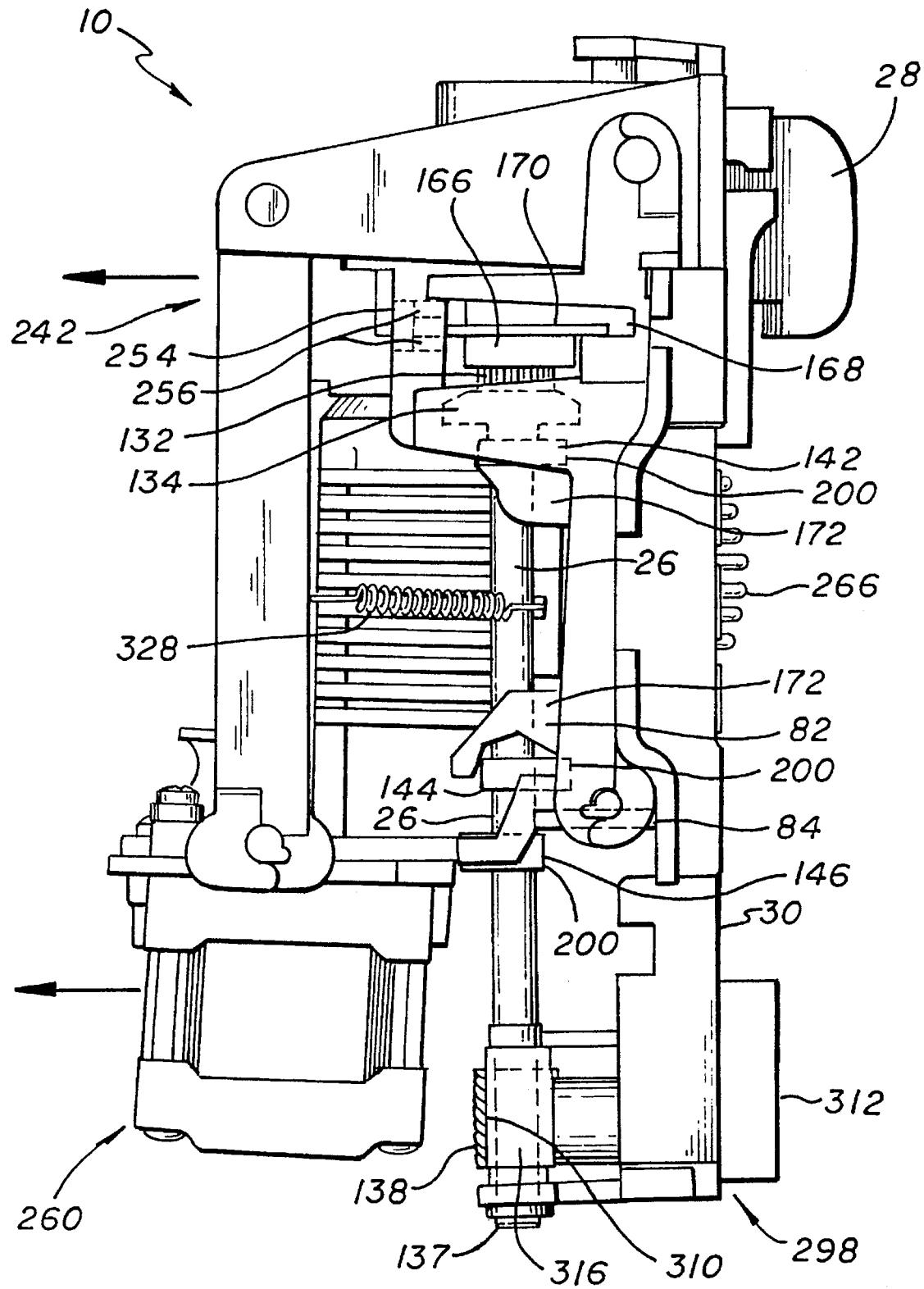
FIG. 12 is a partial, cross-sectional side view of the interlock, latching and retaining mechanism of FIG. 11, shown without the pumping segment.

As the latch arm 28 of the interlock, latching and retaining mechanism 10 is rotated to its open position, a number of things occur (see FIGS. 11 and 12). The straight tooth gear 132 attached to the top end 130 of the shaft 26 cooperates with the gear ring 166 attached to the bottom end 160 of the latch rod 70 to thereby rotate the shaft 26. Also, the wall 170 extending from the outer circumference 168 of the gear ring 166 rotates out from between the spaced apart members 256 of the photo-detector 254 (shown as dashed lines in FIG. 12), to thereby indicate to the infusion system 12 that the latch arm 28 is in an open configuration. As the shaft 26 rotates, the raised portions 200 of the first and second cams 142, 144 lose contact with the second portion 176 of the clamp 32. As the first and second cams 142, 144 lose contact with the clamp 32, the opposing members 172 of the clamp 32 are permitted to pivot about their pegs 190.

Referring primarily to FIG. 11, when the latch arm 28 is rotated to its open position, the shaft 26 cooperates with the flow control actuator 272 to orient the projections 278, 279 extending therefrom so that they may be received by the groove 222 formed in the slider 216 of the pumping segment 14. Significantly, the irregularly shaped projection 279 is adapted to prohibit improper placement of the pumping segment 14 into the clamp 32. Should the pumping segment 14 be placed in the clamp 32 with only a portion of its flange 210 received in the clamping fingers 188 and with the projections 278, 279 not received by the groove 222, upon placing the interlock, latching and retaining mechanism 10 in its closed configuration, the slider 216 will not be moved from its "flow stop" position. The irregularly shaped projection 279 is adapted to interfere with the slider 216 in that the pumping segment 14 cannot be forced within the clamp 32 so that all of its flange 210 is received in the clamping fingers 188 after the interlock, latching and retaining mechanism 10 is placed in its closed configuration. This prevents seating a pumping segment 14 in its "flow stop" position into an infusion system 12 that has been initialized for pumping fluids.

Referring primarily to FIG. 12, as the latch arm 28 is opened, the shaft 26 cooperates with the second end 310 of the second housing 304 of the air-in-line sensor 298. Through this cooperation, the sideways extending projection 312 of the second housing 304 is rotated approximately 90° counterclockwise and away from the front surface 320 of the first housing 300.

When these actions occur, the pumping segment 14 can be placed within the clamping fingers 188 of the clamp 32 (see FIG. 11). The pumping segment 14 is oriented so that its proximal end 202 sits closest to the top 44 of the faceplate 30 and so that its flanges 210 are held between the clamping fingers 188 and the front side 60 of the faceplate 30. Further, the pumping segment 14 is oriented so that the groove 222 formed in the slider 216 receives the flow control actuator projections 278 and 279 so that the ears 228 formed into the slider 216 are aligned with the cut-outs 292 formed in the curtain 286. In order to so orient the slider 216, it must be placed in its flow stop position, which is where the slider 216 is moved towards the distal end 204 of the pumping segment 14.

Additionally, when the pumping segment 14 is placed within the clamp 32, the intermediate section 236 of the pumping segment 14, where the cover 234 provides access to the membrane 230, is placed in alignment with the pump fingers aperture 106. Moreover, the dome shaped pressure vessel 238 of the pumping segment 14 is placed in alignment with the pressure sensor 284. Finally, the conventional tubing 334 which is attached to the cylindrical tubing fitting 208 formed on the distal end 204 of the pumping segment 14 is placed adjacent the front surface 320 of the first housing 300.

Also, as the latch arm 28 is rotated to its open position, the raised portion 200 of the third cam 146 of the shaft 26 rotates and engages the the frame 242. By so engaging the frame, the third cam 146 causes the frame 242 to retract away from the faceplate 30.

As the frame 242 retracts away from the faceplate 30 the degree to which the fingers 266 of the peristaltic pumping mechanism 260 extend through the pump fingers aperture 108 is decreased. This is significant because, when the fingers 266 are caused to recede, they are retracted from their operational position.

After the pumping segment 14 is placed within the clamp 32, the latch arm 28 can be rotated to its closed position. When the latch arm 28 is rotated to its closed position, the previously described interactions between the interlock, latching and retaining mechanism 10 and the other components of the infusion system 12 occur in reverse. Once the latch arm 28 is rotated to its closed position (not shown), the frame 242 moves back towards the faceplate 30 and, by way of its engagement with the first and second cams 142, 146 of the shaft 26, the clamp 32 is prevented from pivoting and thereby securely holds the pumping segment 14 in place. Furthermore, the peristaltic pumping mechanism 260 is placed in operating position so that the at least one of the fingers 266 occludes flow through the pumping segment 14 and all fingers 266 are engaged to peristaltically pump fluid through the pumping segment 14. Also, the sideways extending projection 312 of the air-in-line sensor 298 rotates to retain the conventional tubing 334 between itself and the front surface 320 of the first housing 300 to thereby be placed in operating position for monitoring of the fluid. Additionally, the conventional tubing 334 extending from the proximal end 202 of the pumping segment 14 is retained between the "head" and "tail" of the g-shaped latch arm 28.

Moreover, the flow control actuator 272 is rotated, thereby moving the slider 216 to the proximal end 202 of the pumping segment 14, a position where maximum flow through the pumping segment 14 is permitted. As the slider 216 so moves, the ears 228 slide behind the downwardly directed portions 290 of the curtain 286. Finally, when the latch arm 28 is closed, a proper interface between the domed-shaped pressure vessel 238 and the pressure sensor 284 is created and the wall 170 extending from the outer circumference 168 of the gear ring 166 travels within the photodetector 254, thereby interrupting the light energy transmitted by the detector 254 and indicating to the infusion system 12 that the latch arm 28 is closed.

The timing of the interactions described above is critical. In particular, the interlock, latching and retaining mechanism 10, functions to place at least one finger 266 of the peristaltic pumping mechanism 260 in a position to occlude fluid flow prior to causing the slider 216 of the pumping segment 14 to move to a position for allowing fluid flow. In this way, undesired free flow conditions are avoided. Additionally, the interlock, latching and retaining mechanism 10 operates to ensure proper sequencing of operation by placing fluid line monitoring structure 22, i.e., air-in-line sensing, as well as the pumping structure 18 of the infusion system 12 into operating position contemporaneously with the clamp 32 securely holding the pumping segment 14 and the gear ring 266 causing the photodetector 254 to communicate to the infusion system 12 that the latch arm 28 is being closed.

Finally, when the latch arm 28 is rotated again to its open position (not shown), the pumping segment 14 is ejected from the interlock, latching and retaining mechanism 10. In order to eject the pumping segment 14, the "head" of the g-shaped latch arm 14 engages the conventional tubing 234 attached to the cylindrical tubing 206 formed at the proximal end 202 of the pumping segment 14. This engagement, in conjunction with the ejecting forces applied against the pumping segment 14 by the pumping fingers 216, overcomes the opposing forces retaining the pumping segment 14 against the faceplate 30 supplied by the springs 328 attached to the clamp 32, which biases the clamp 32 to a "closed" position. When these opposing forces are overcome, the members 172 of the clamp 32 pivot to an "open" position, thereby releasing the flange 210 of the pumping segment 14 from the clamping fingers 32 and causing the pumping segment 14 to "pop" out of the interlock, latching and retaining mechanism 10.

Although the present invention has been described as cooperating with a pumping segment having a particular design, the interlock, latching and retaining mechanism may be appropriately configured to cooperate with other pumping segment designs and may be adapted to cooperate with a wide range of segments for fluid flow. Additionally, the present invention is contemplated to be incorporated into an infusion system lacking one or more of pumping, flow control and fluid monitoring structures.

Therefore, the interlock, latching and retaining mechanism 10 functions, through the manipulation of the single latch arm 26, to quickly, reliably and simply load the pumping segment 14 for fluid flow into the infusion system 12 as well as load pumping 18, flow control 16 and fluid line monitoring structures 22 into engagement with the pumping segment 14.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An interlock, latching and retaining mechanism for placing an infusion set into operating position on an infusion system having fluid flow control and pumping structure, comprising:

a faceplate;

a latch arm, said latch arm being rotatably mounted to said faceplate; and means cooperating with said latch arm and said faceplate for placing the infusion set into operating position with the fluid flow control and pumping structure of the infusion system, wherein said cooperating means includes a shaft adapted to rotate in response to movement of the latch arm and place the infusion set into operating position with the fluid flow control and pumping structure of the infusion system.

2. An interlock, latching and retaining mechanism for placing an infusion set into operating position on an infusion system having fluid line monitoring and flow control structure, comprising:

a faceplate;

a latch arm, said latch arm being rotatably mounted to said faceplate; and means cooperating with said latch arm and said faceplate for placing the infusion set into operating position with the fluid line monitoring and flow control structure of the infusion system, wherein said cooperating means includes a shaft adapted to rotate in response to movement of the latch arm and place the infusion set into operating position with the fluid line monitoring and flow control structure of the infusion system.

3. An interlock, latching and retaining mechanism for placing an infusion set into operating position on an infusion system having fluid line monitoring and pumping structure, comprising:

a faceplate;

a latch arm, said latch arm being rotatably mounted to said faceplate; and means cooperating with said latch arm and said faceplate for placing the infusion set into operating position with the fluid line monitoring and pumping structure of the infusion system, wherein said cooperating means includes a shaft adapted to rotate in response to movement of the latch arm and place the infusion set into operating position with the fluid line monitoring and pumping structure of the infusion system.

4. An interlock, latching and retaining mechanism for placing an infusion set into operating position on an infusion system having fluid line monitoring, flow control and pumping structure, comprising:

a faceplate;

a latch arm, said latch arm being rotatably mounted to said faceplate; and means cooperating with said latch arm and said faceplate for placing the infusion set into operating position with the fluid line monitoring, flow control and pumping structure of the infusion system, wherein said cooperating means includes a shaft adapted to rotate in response to movement of the latch arm and place the infusion set into operating position with the fluid line monitoring, flow control and pumping structure of the infusion system.

5. The interlock, latching and retaining mechanism of claim 4, wherein said cooperating means includes a clamp to hold a fluid flow segment of the infusion set in engagement with the fluid line monitoring, flow control and pumping structure of the infusion system.

6. The interlock, latching and retaining mechanism of claim 4, wherein said cooperating means places the pumping structure into operating position prior to placing the flow control structure into operating position to thereby avoid free flow conditions.

7. The interlock, latching and retaining mechanism of claim 4, wherein the infusion system includes an air-in-line sensor and said cooperating means places the infusion set into operating position with said air-in-line sensor by rotating said air-in-line sensor into and out of operating position with the infusion set.

8. The interlock, latching and retaining mechanism of claim 4, wherein said shaft includes a plurality of camming and gearing surfaces which interact with the fluid line monitoring, flow control and pumping structure of the infusion system.

9. An interlock, latching and retaining mechanism for an infusion set comprising:

a faceplate having a plurality of apertures formed therethrough;

a latch arm rotatably mounted to said faceplate and extending through a first aperture of said plurality of apertures formed in said faceplate;

a clamp having two opposing members, said clamp pivotably mounted to a rear surface of said faceplate, said opposing members extending through a second aperture of said plurality of apertures formed in said faceplate;

a shaft having a plurality of camming surfaces, said shaft being rotatably attached to said rear surface of said faceplate, said shaft adapted to be rotated by said latch arm; and a first camming surface of said plurality of camming surfaces adapted to lock and unlock said clamp.

10. The interlock, latching and retaining mechanism as recited in claim 9, wherein a terminal end of said opposing members includes a plurality of fingers, said fingers adapted to releasably hold a fluid flow segment.

11. The interlock, latching and retaining mechanism as recited in claim 9, further comprising spring means for biasing said clamp in a closed configuration.

12. The interlock, latching and retaining mechanism as recited in claim 9, wherein said shaft includes a plurality of gearing surfaces.

13. The interlock, latching and retaining mechanism as recited in claim 12, wherein said latch arm includes a latch gear surface, said latch gear surface adapted to cooperate with a first gear surface of said plurality of gearing surfaces of said shaft.

14. The interlock, latching and retaining mechanism as recited in claim 13, wherein a second gear surface of said plurality of gearing surfaces of said shaft engages a flow control structure mounted to said faceplate.

15. The interlock, latching and retaining mechanism as recited in claim 14, wherein a third gear surface of said plurality of gearing surfaces of said shaft engages an air-in-line sensing structure mounted to said faceplate.

16. A mechanism for placing an infusion set into operating position on an infusion system capable of performing a plurality of functions, comprising:

a faceplate;

a latch arm, said latch arm being rotatably attached to said faceplate; and means cooperating with said latch arm and said faceplate for placing the infusion set into operating position with the infusion system, wherein said cooperating means includes a shaft adapted to rotate in response to movement of the latch arm and place the infusion set into operating position.

17. A mechanism for placing an infusion set into operating position on an infusion system having a plurality of functions including an air-in-line sensor, comprising:

a faceplate;

a latch arm, said latch arm being rotatably attached to said faceplate; and means cooperating with said latch arm and said faceplate for placing the infusion set into operating position with the infusion system, wherein said cooperating means places the infusion set into operating position with said air-in-line sensor by rotating said air-in-line sensor into operating position with the infusion set.

18. A mechanism for placing an infusion set into operating position on an infusion system having a fluid pumping device and a flow stop device, comprising:

a faceplate;

a latch arm, said latch arm being rotatably attached to said faceplate; and means cooperating with said latch arm and said faceplate for placing the infusion set into operating position with the fluid pumping device of the infusion system prior to placing the fluid stop device in a position for allowing flow, so as to avoid free flow conditions.

19. The mechanism of claim 18, wherein the cooperating means places the flow stop device into a flow stop position so the infusion set is occluded prior to disengaging the fluid segment from the pumping device.

20. The mechanism of claim 19, wherein the infusion set includes fluid line monitoring structure and said cooperating means operates to place the fluid line monitoring structure into operating position contemporaneously with placing the fluid pumping structure into operating position.

21. The mechanism of claim 20, wherein the fluid line monitoring structure includes an air-in-line sensor and said cooperating means places the infusion set into operating position with said air-in-line sensor by rotating said air-in-line sensor.

22. A mechanism for placing an infusion set into operating position on an infusion system having a plurality of functions, comprising:

a faceplate;

a latch arm, said latch arm being rotatably attached to said faceplate; and means cooperating with said latch arm and said faceplate for placing the infusion set into operating position with the infusion system, wherein said cooperating means includes a clamp responsive to movement of the latch arm that holds a fluid flow segment of the infusion set in a predetermined position.

23. The mechanism of claim 22, wherein said clamp includes spring-loaded fingers that engage the fluid flow segment to position the segment into the operating position.

24. The mechanism of claim 23, wherein actuation of said latch arm causes said spring-loaded fingers to alternatively assume locked and unlocked configurations.

25. The mechanism of claim 23, wherein the infusion system includes an air-in-line sensor and said cooperating means are also for rotating said air-in-line sensor into operating position with said infusion set.

26. A mechanism for placing an infusion set into operating position on an infusion system capable of performing a plurality of functions, the infusion set including tubing for fluid flow, said mechanism comprising:

a faceplate; and a latch arm having a slot, said latch arm being rotatably attached to said faceplate and having an open position and a closed position;

wherein said slot engages and retains tubing when said latch arm is in the closed position.

27. The mechanism of claim 26, further comprising means cooperating with said latch arm and said faceplate for placing the infusion set into operating position with the infusion system, wherein the infusion system includes an air-in-line sensor and said cooperating means places the infusion set into operating position with said air-in-line sensor by rotating said air-in-line sensor.

28. The mechanism of claim 26, further comprising a clamp responsive to actuation of the latch arm for holding a fluid flow segment of the infusion set in operating position with the infusion system.

29. The mechanism of claim 28, wherein said clamp includes a plurality of spring-loaded fingers that engage the fluid flow segment.

30. The mechanism of claim 29, wherein said latch arm includes locking means responsive to movement of said latch arm, said locking means causing said spring-loaded fingers to assume a locked configuration when said latch arm is in the closed position and to assume an unlocked configuration when said latch arm is in the open position.

31. A mechanism for placing an infusion set into operating position with an infusion system having a flow control mechanism, comprising:

a faceplate;

a latch arm, said latch arm being rotatably attached to said faceplate; and means cooperating with said latch arm and said faceplate for placing the infusion set into operating position with the infusion system, wherein said cooperating means includes means for retracting the flow control mechanism of the infusion system away from said faceplate so as to place the flow control mechanism out of operating position with the infusion set.

32. The mechanism of claim 31, wherein the infusion system includes an air-in-line sensor and said cooperating means places the infusion set into and out of operating position with said air-in-line sensor by rotating said air-in-line sensor.

33. The mechanism of claim 31, wherein said cooperating means includes a clamp having an open position and a closed position, said clamp adapted to receive the infusion set when placed in the open position and adapted to hold the infusion set in operating position with the infusion system when placed in the closed position.

34. The mechanism of claim 33, wherein said clamp includes spring-loaded fingers that engage and hold the infusion set in operating position with the infusion system.

35. The mechanism of claim 34, wherein said latch arm includes locking means responsive to said latch arm, said locking means causing said spring-loaded fingers to assume a locked configuration when said latch arm is in the closed position and to assume an unlocked configuration when said latch arm is in the open position.

36. A flow control system for an infusion system that operates to transfer fluid through a conduit to a patient, comprising:

an infusion segment having a slider with a first position and a second position, said slider allowing fluid flow when placed in the first position and stopping fluid flow when placed in the second position; and a rotating actuator mounted on the infusion system for engaging the slider, said actuator including an engaging device configured to interface with the slider;

wherein as said actuator rotates said slider is alternatively placed in the first and second positions.

37. The flow control system of claim 36, wherein said segment includes a slot closed at one end for receiving the engaging device.

38. A method for controlling the infusion of a fluid to a patient through an infusion set having a pumping segment and a flow stop device in engagement with the infusion set, said flow stop device having a flow position allowing flow through the infusion set and a flow stop position at which the infusion set is occluded, said infusion set configured for engagement with a pumping device, said pumping device occluding the pumping segment when the pumping segment is in the operating position, the method comprising the steps of:

mounting the pumping segment to the pumping device;

moving a latch arm to a closed position;

wherein the step of moving the latch arm to the closed position comprises the steps of:

moving the pumping segment into the operating position with the pumping device so that the pumping device occludes the pumping segment, and thereafter;

moving the flow stop device to the flow position.

39. The method of claim 38 further comprising the steps of:

moving the latch arm to an open position;

wherein the step of moving the latch arm to the open position comprises the steps of:

moving the flow stop device to the flow stop position; and thereafter moving the pumping segment into a non-operating position with the pumping device so that the pumping device no longer occludes the pumping segment.

40. The method of claim 38 further comprising the step of engaging a portion of the infusion set adjacent the pumping segment with the latch arm when the latch arm is moved to the closed position to confine the infusion set to a predetermined position.

41. The method of claim 40 further comprising the step of disengaging the portion of the infusion set when the latch arm is moved to the open position to allow removal of the infusion set.

42. The method of claim 38 wherein the step of moving the latch arm to the closed position further comprises the step of rotating an air-in-line sensor into an operating position in relation to the infusion set.

* * * * *